(12) United States Patent
Tsutsumi

(10) Patent No.: US 7,867,455 B2
(45) Date of Patent: Jan. 11, 2011

(54) MICROTUBE PICKING DEVICE FOR PHARMACEUTICAL DEVELOPMENT

(75) Inventor: Kazuhiro Tsutsumi, Osaka (JP)

(73) Assignee: Tsubakimoto Chain Co., Osaka (JP)

( * ) Notice: Subject to any disclaimer, the term of this patent is extended or adjusted under 35 U.S.C. 154(b) by 173 days.

(21) Appl. No.: 12/043,167

(22) Filed: Mar. 6, 2008

(65) Prior Publication Data
US 2008/0267826 A1 Oct. 30, 2008

(30) Foreign Application Priority Data
Apr. 24, 2007 (JP) .............................. 2007-114156

(51) Int. Cl.
*B01L 99/00* (2010.01)
(52) U.S. Cl. .................... 422/104; 422/99; 422/102
(58) Field of Classification Search ................ 422/102, 422/104; D24/224, 227–230
See application file for complete search history.

(56) References Cited

U.S. PATENT DOCUMENTS

| | | | |
|---|---|---|---|
| D290,401 S | * | 6/1987 | Bjorkman .................. D24/227 |
| 4,740,025 A | | 4/1988 | Nelson |
| 5,372,786 A | * | 12/1994 | Iles ............................ 422/104 |
| 5,407,640 A | * | 4/1995 | Iles ............................ 422/104 |
| 5,651,941 A | | 7/1997 | Stark |
| 5,885,530 A | * | 3/1999 | Babson et al. ................ 422/65 |
| 5,948,360 A | | 9/1999 | Rao |
| 5,952,218 A | * | 9/1999 | Lee et al. .................. 435/288.7 |
| 5,985,219 A | | 11/1999 | Lind |
| 2007/0017885 A1 | | 1/2007 | Taike |

FOREIGN PATENT DOCUMENTS

| | | |
|---|---|---|
| EP | 1 745 850 | 1/2007 |
| JP | 59-9692 | 3/1984 |
| JP | 04-009668 | 1/1992 |
| JP | 06-510233 | 11/1994 |
| JP | 11-230969 | 8/1999 |
| JP | 2004-223646 | 8/2004 |
| JP | 2006-214919 | 8/2006 |
| WO | WO 96/27442 | 9/1996 |
| WO | WO 2005/102617 | 11/2005 |

OTHER PUBLICATIONS

Translation of Japanese Search Report Dated Aug. 11, 2009.
Translation of the Description of Fig. 3 in JP 59-9692.

* cited by examiner

*Primary Examiner*—Jill Warden
*Assistant Examiner*—Shogo Sasaki
(74) *Attorney, Agent, or Firm*—Dann, Dorfman, Herrell and Skillman; Henry H. Skillman

(57) ABSTRACT

A microtube picking device for pharmaceutical development in which the picking of a selected microtube from a storage rack can be reliably carried out without producing friction in a latch member and without shifting the position of the microtube when it is reinserted into the storage rack. The microtube picking device has a picking member with a microtube accommodating hole whose internal surfaces are arranged in a polygonal array. The device also has at least one latch member having elastic force, which presses and fixes the microtube to two adjacent surfaces of the microtube accommodating hole.

5 Claims, 5 Drawing Sheets

MICROTUBE PICKING DEVICE FOR PHARMACEUTICAL DEVELOPMENT

FIELD OF INVENTION

The present invention relates to a microtube picking device for pharmaceutical development suitable for taking out or taking in a selected microtube accommodated in a storage rack in high density in a field of pharmaceutical development, study and the like.

BACKGROUND OF THE INVENTION

In a field of pharmaceutical development, study and the like, a storage and a transfer have been carried out by sealing a sample-solved solution into a vessel called a microtube having an upper part and a lower part. The upper part is larger in outline than the lower part. A plurality of the microtubes stand vertically in a storage rack, defined as a grid shape, for example a storage rack defined into 96 in 8 rows and 12 columns (hereinafter referred to as "96 tube racks") to accommodate them. Further, a storage rack having a total defined number of 384 microtube in 16 rows and 24 columns (hereinafter referred to as "384 tube racks") has been also known to accommodate smaller microtube.

As a microtube picking device for pharmaceutical development for taking a selected microtube out of or into such a 96 tube racks or 384 tube racks, a microtube picking device 500 for pharmaceutical development as shown in FIG. 9 has been known. This microtube picking device 500 for pharmaceutical development has insertion holes 532, into which the microtube are loosely supported. The insertion holes have a cross section smaller than the upper parts and larger than the lower parts of the microtube which fit to a lower part of the microtube 510 to support the microtube, and are formed in a storage rack 530. The picking device 500 has a plunger member 540 which may be protruded to displace a selected microtube 510 directly above through the insertion hole 532 of the storage rack 530 by abutting the bottom surface of the microtube 510. The plunger member is at a lower position than the storage rack 530, and a concurrently-lifting prevention member 560 is positioned above the top surfaces of the surrounding microtube so that the microtube pushed up with the plunger member 540 does not lift the surrounding microtube together exists at upper position than microtube 510. The microtube picking device 500 has opposed gripping members 522, which provide a space slightly smaller in size than the size of the upper part of the protruded up microtube 510 and sandwich the microtube between the opposed gripping members to grip the microtube 510 which was advanced in accordance with a protrusion-up operation by the plunger member 540 under the microtube 510 by allowing the space between the resilient gripping members 522 to be narrowed to accommodate the microtube. The microtube picking device 500 also has a dispensing plunger member 550, which discharges the microtube 510 gripped by the picking member 520. The material of a resilient gripping members 522 is preferably a plastic such as polypropylene having sufficient elastic force at a very low temperature to grip the microtube. (See FIG. 1 of Japanese Laid-Open Patent Publication No. 2006-214919)

It is generally the practice, when using the 384 tube racks, to form a closure on the microtube by fusion-welding an aluminum foil to an opening portion of the top of the microtube. A small tab portion of the aluminum foil is extended beyond a wall of the opening of the microtube. Thus there is a problem that the tab portion causes friction to occur with the resilient gripping member 522.

Further, since the gripping members 522 are provided on both sides of the microtube 510 and are deflected, unbalance occurs in the respective amounts of deflections of the members 522 and the microtube become off-center and the position of the microtube 510 is not kept properly centered. Thus since the position of the microtube 510 is shifted, the microtube 510 cannot be re-inserted into the storage rack 530.

Further, since the sandwich directions of the gripping members 522 are directed to opposed two surfaces, the microtube sometimes is inclined to a direction perpendicular to the surfaces. As a result a phenomenon that the microtube 510 cannot be re-inserted into the storage rack 530 occurs.

SUMMARY OF THE INVENTION

Accordingly, one object of the present invention is to provide a microtube picking device for pharmaceutical development in which the picking of a microtube can be reliably carried out without producing friction in a gripping member and without shifting the centered position of the microtube.

The invention solves the above-mentioned problems by a providing a microtube picking device for pharmaceutical development having a picking member, which clamps a microtube, which seals a sample for pharmaceutical development, when a selected one microtube is taken out of a storage rack, which vertically accommodates a plurality of microtube in a matrix manner and accommodates a microtube at a predetermined accommodation position in said storage rack, characterized in that said picking member has a microtube accommodating hole whose internal surfaces are disposed in a polygonal array and has at least one latch member having elastic force, which presses and fixes said microtube to two adjacent opposite surfaces of the microtube accommodating hole.

One of the embodiments of the invention further solves the abovementioned problems by attaching a latch member to each of two adjacent surfaces of the microtube accommodating hole, one for each of the two opposite surfaces.

The invention further solves the above-mentioned problems by forming the latch member of metal.

If metal used in the latch member has sufficient elastic force, the metal is not limited. However, as such metals are expensive, an easily workable steel is preferably used.

In a microtube picking device for pharmaceutical development having a picking member, which clamps a microtube which seals a sample for pharmaceutical development, when a selected one microtube is taken out of a storage rack, which vertically accommodates a plurality of microtube in a matrix manner and accommodates a microtube at a predetermined accommodation position in said storage rack, said picking member has a microtube accommodating hole whose internal surface is a polygon and has at least one latch member having elastic force, which presses and fixes said microtube to adjacent two surfaces of the microtube accommodating hole, the microtube is positioned by being abutted on the adjacent two surfaces, which are reference surfaces of the microtube accommodating hole. Thus the microtube does not incline and is clamped at the same position in the microtube accommodating hole. Further, since the clamping position and the clamping stance of the microtube are constant, the microtube can be reinserted into a storage rack.

In the embodiment in which two latch members face the adjacent reference surfaces of the microtube accommodating hole respectively, the same magnitude force is applied by the two latch members, and due to the relationship between action and reaction, a uniform force is applied to the clamped microtube from the all directions. Thus the microtube can be stabilized when being inserted into the storage rack.

When the latch member is formed of metal, if the latch member collides with a tab of an aluminum foil covering the opening portion of the microtube, it does not produce friction. Thus the endurance of the latch member is improved.

Figure 1:
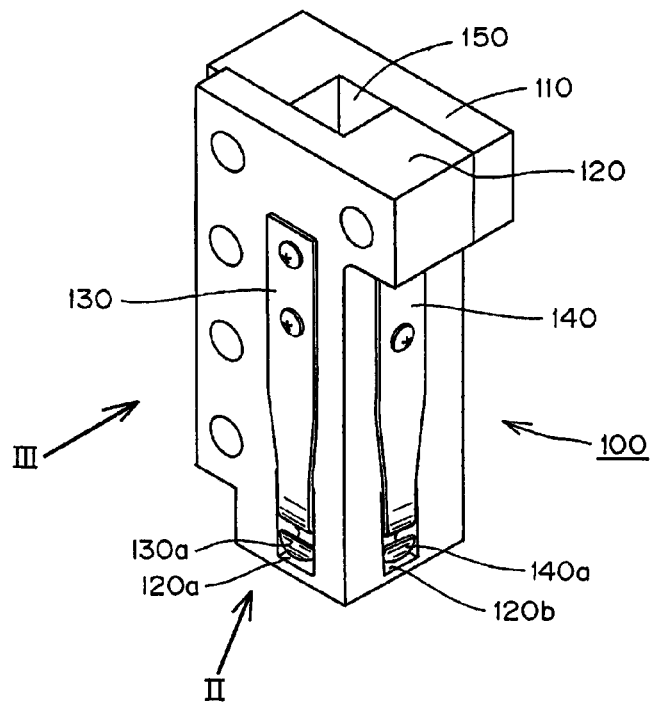
FIG. 1 is a perspective view of a picking member of a microtube picking device for pharmaceutical development according to example 1.
Figure 2:
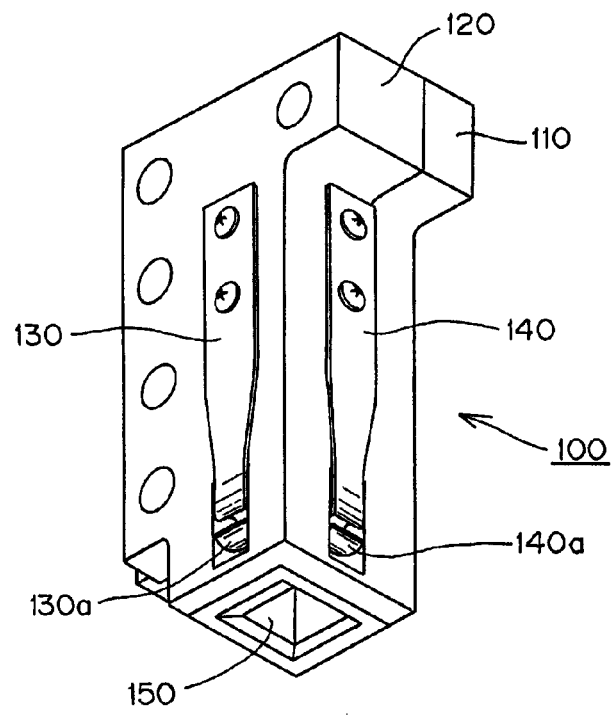
FIG. 2 is a perspective view of the picking member shown in FIG. 1 viewed from a direction of an arrow II.
Figure 3:
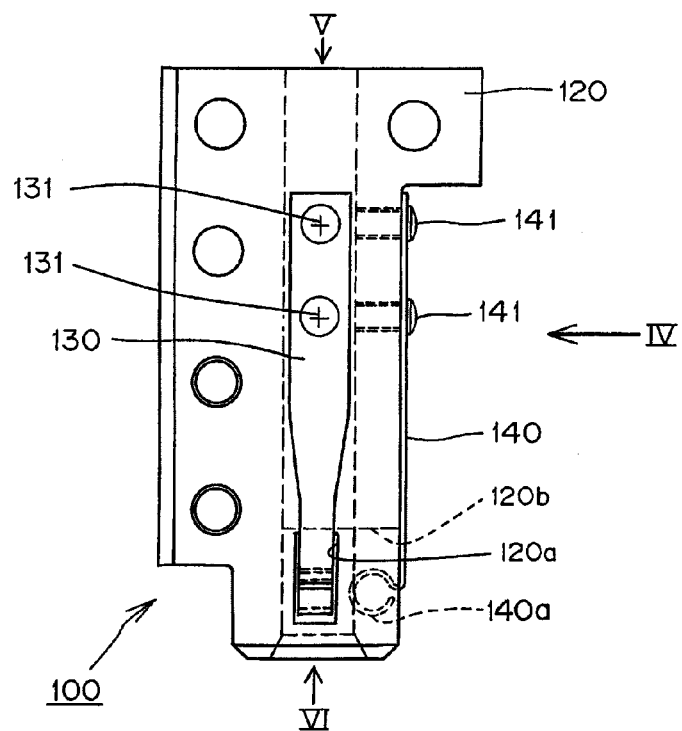
FIG. 3 is a front view of the picking member shown in FIG. 1 viewed from a direction of an arrow III.

DESCRIPTION OF PREFERRED
EMBODIMENTS OF THE INVENTION

The present invention comprises a microtube picking device for pharmaceutical development having a picking member, which grips a microtube containing a sample for pharmaceutical development, so that a selected one microtube may be taken out of a storage rack, which vertically accommodates a plurality of microtube in a matrix manner and accommodates the selected microtube at a predetermined accommodation position in said storage rack. The picking member has a microtube-accommodating hole which may be registered with the predetermined accommodation position. The internal surfaces of the hole form a polygon and are provided with at least one latch member having elastic force, which presses and fixes said microtube to adjacent two reference surfaces of the microtube accommodating hole at the predetermined accommodation position. The present invention provides a microtube picking device for pharmaceutical development in which a latch member does not shift the insertion position of the selected microtube in the storage rack and picking and reinsertion of the microtube can be reliably performed. Any concrete form of the picking device or other configurations and the like may be used. Preferably the polygonal hole has two adjacent internal angularly-related reference surfaces which are rigid and are fixed to define the predetermined accommodation position of the selected microtube. The at least one latch member confronts the reference surfaces and biases the microtube into its accommodation position.

Example 1

FIGS. 1-7 illustrate a first example of a picking member 100 used in a microtube picking device for pharmaceutical development according to the present invention, The member comprises a pair of side members, a reference side member 110 and an opposite side member 120 having an L-shaped cross-sections fixed together to provide a microtube accommodating hole 150 whose combined internal portion is a box space of a square cross section. The side member 120 is a latch supporting member, which supports two latch members 130 and 140 formed as leaf springs of steel iron.

Figure 4:
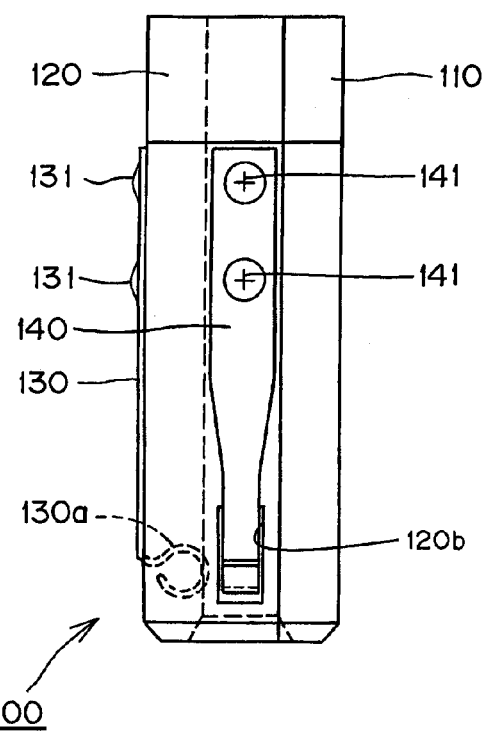
FIG. 4 is a side view of the picking member shown in FIG. 3 viewed from a direction of an arrow IV.
Figure 7:
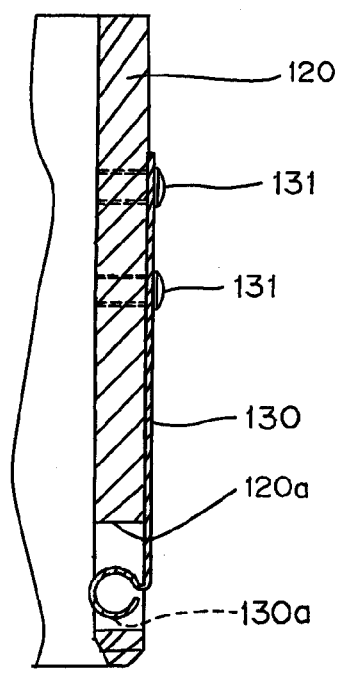
FIG. 7 is a fragmentary cross section taken on the line VII-VII of FIG. 5.

The latch member 140 has a free end circularly bent end 130a as shown in FIG. 7 and by a hidden line in FIG. 4. The latch member 140 has the same shape as the latch member 130 as shown by a hidden line in FIG. 3. The end circular portions 130a and 140a of these latch members 130 and 140 are respectively protruded past the interior surface into the microtube accommodating hole 150 through insertion orifices 120a and 120b provided below a portion where the latch members 130 and 140 of the latch supporting opposite side member 120 are adhered above the orifices 120a and 120b, for example by fasteners 131 and 141 It is noted that the hole 150 is open at the top and at the bottom. When the microtube is inserted upwardly into the microtube accommodating hole 150, the latch slides over the upper part, past the junction between the upper part and the lower part and engages against the lower part, and when the microtube is pushed downwardly out of the microtube accommodating hole 150 for reinsertion into a rack, the above-mentioned configuration of the latch members 130 and 140 can smoothly slide over the junction and the upper part of the microtube.

Figure 5:
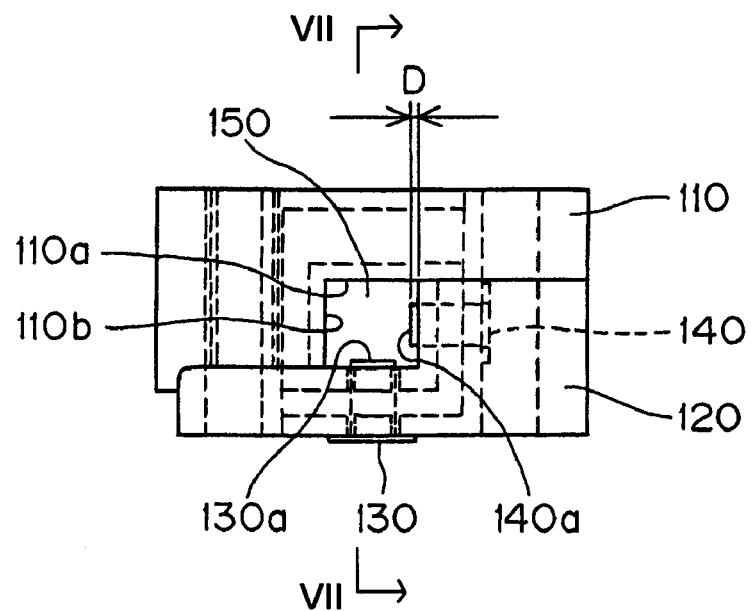
FIG. 5 is a top view of the picking member shown in FIG. 3 viewed from a direction of an arrow V.
Figure 6:
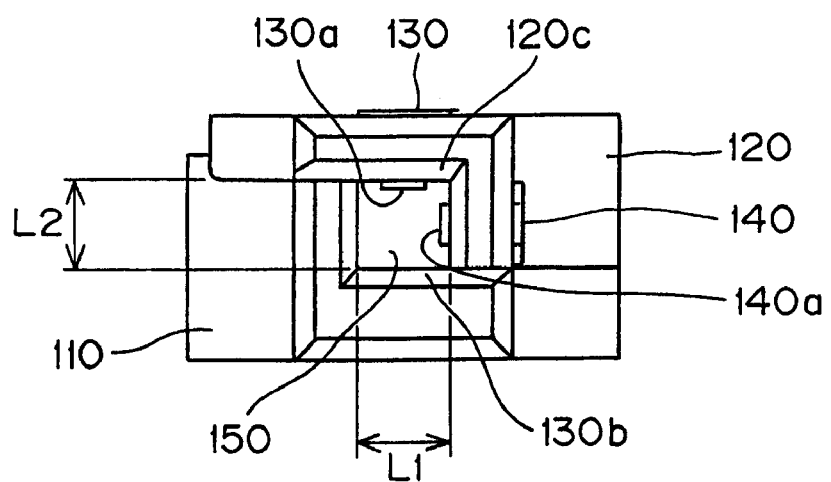
FIG. 6 is a bottom view of the picking member shown in FIG. 3 viewed from a direction of an arrow VI.

Since in example 1, a horizontal cross-sectional shape of the microtube is a square of 4.3 mm, per side, the shape of an internal surface of the microtube accommodating hole 150 is set to a square of L1=L2=4.4 mm, per side, as shown in FIG. 6. As shown in FIG. 5, the top end circular portions 130a and 140a of the latch members 130 and 140 are protruded inside the microtube accommodating hole 150 by D=0.5 mm. That is when a microtube is advanced into the microtube accommodating hole 150 through an internal portion at a lower end of a picking member 100 in accordance with a protrusion-up operation by a protrusion-up member of a microtube picking device for pharmaceutical development, the free end circular portions 130a and 140a are respectively retracted backward by 0.4 mm and the microtube is pressed against two reference surfaces 110a and 110b forming a microtube accommodating hole 150 of the reference side member 110, which crosses at a right angle, so that the microtube can be held at a correct position without being inclined or fallen down.

At the bottom of the microtube accommodating hole 150 as shown in FIG. 6, the opposite side members 120 have tapered portions 120c and 130b to facilitate the operation when the microtube in the is taken in or taken out of the microtube accommodating hole 150. Therefore the coming in and going of the microtube becomes smooth.

Although there are different configurations of parts of the microtube picking device other than the picking member, the picking members are basically the same as the illustrated microtube picking device for pharmaceutical development, The description of the different configurations of other parts are omitted. Further, although a resilient metallic leaf spring is utilized in example 1, if there is room for it, a coil spring may be combined with a plate to produce the pressing of the microtube against the two opposite surfaces of the microtube accommodating hole.

Example 2

Example 2, which is another embodiment according to the present invention, will be described with reference to FIG. 8.

Figure 8:
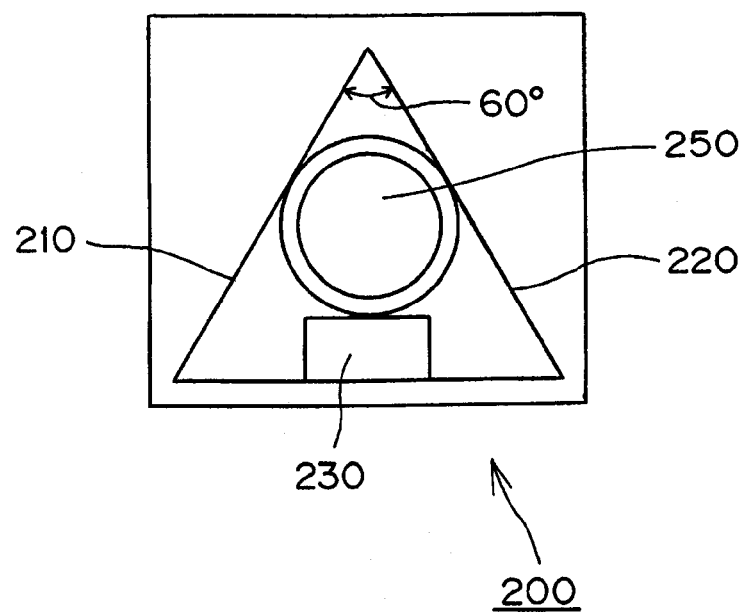
FIG. 8 is a top view of a picking member of a microtube picking device for pharmaceutical development according to example 2.
Figure 9:
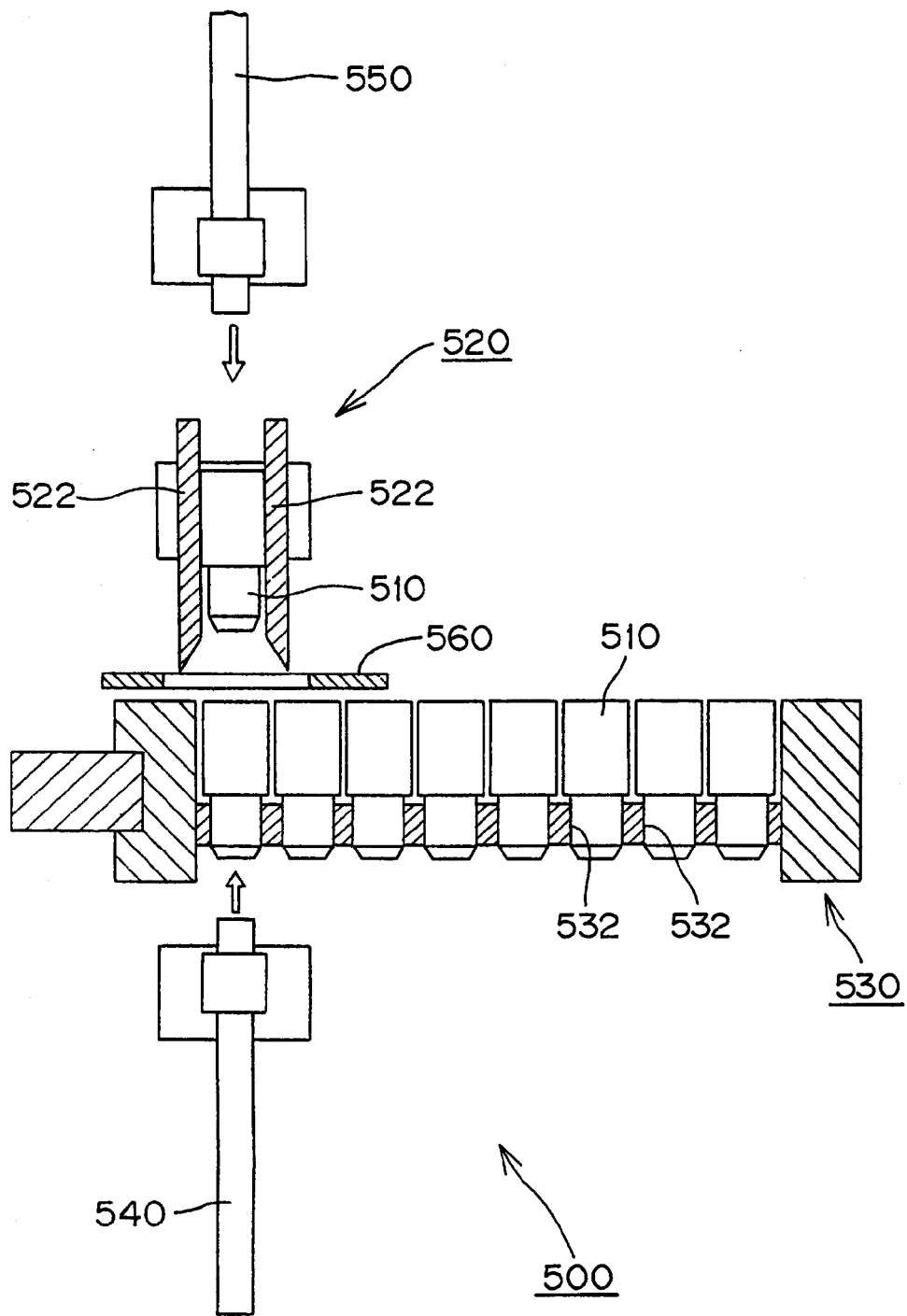
FIG. 9 is a diagrammatic view explaining a prior art microtube picking device.

FIG. 8 is a top view of a picking member 200 in example 2. This picking member 200 has a target of a cylindrical microtube 250. The micro-tube-receiving hole of the member 200 is formed by surfaces arrayed in a triangular orientation, and uses two surfaces at 60 degrees as reference surfaces 210 and 220. The microtube 250 is clamped by pressing the microtube 250 against the reference surfaces 210 and 220 in a direction by a spring member 230, which is mounted on the third wall opposite the corner between the two reference surfaces, and enters the hole through an orifice in the third wall. In this case the microtube can be held at a correct position without being inclined. 141 When the microtube is inserted upwardly into the microtube accommodating hole, the latch member 230 slides over the upper part, past the junction between the upper part and the lower part and engages against the lower part, and when the microtube is pushed downwardly out of the microtube accommodating hole for reinsertion into a rack, the latch member 230 can smoothly slide over the junction and the upper part of the microtube as in example 1.

According to the microtube picking device for pharmaceutical development of the present invention, reliable taking out and accommodation operation of a microtube accommodated in a 384 tube rack, which have been difficult, is not only realized but also the technical idea can be applied to a tube-shaped vessel other than the microtube. The industrial applicability is very high.

The invention claimed is:

1. A microtube picking device having a picking member, wherein
said picking member has a square microtube accommodating hole formed by a reference side member having an L-shaped cross-section with two adjacent internal surfaces at right angles and an opposing side member having an L-shaped cross-section with two internal surfaces at right angles, said opposing side member having two leaf spring latch members, each leaf spring latch member being secured at one end to said opposing side member and having a circular free end, said opposing side member having two orifices, one orifice in each of said internal surfaces of said opposing side member, each orifice accommodating the circular free end of one leaf-spring latch member, said reference side member and said opposing side member engaging each other, so that their internal surfaces form said square microtube accommodating hole, said hole having four internal surfaces disposed in a square arrangement,
each leaf-spring latch member biasing said free circular end into and through said microtube accommodating hole, whereby said circular end enters said square microtube accommodating hole, and presses and fixes the accommodated microtube against one of two adjacent internal surfaces of the reference side member of the microtube accommodating hole.

2. A microtube picking device according to claim 1, wherein said leaf-spring latch member is formed of metal.

3. A microtube picking device according to claim 1, wherein said microtube accommodating hole is open at the top and bottom, and one end of said side members have tapered end portions to facilitate the insertion and removal of the microtubes.

4. A microtube picking device according to claim 3, wherein said tapered end portions are at the bottom of said microtube accommodating hole and said one end of the leaf spring latch member is secured to the opposite side wall above the orifice of said opposite side wall, so that the circular free end of said leaf spring latch member is positioned in said orifice between said one end and said tapered end portion of the opposite side wall.

5. A microtube picking device according to claim 1, wherein said two internal surfaces of said reference side member are rigidly fixed to define a predetermined accommodation position within the square microtube accommodating hole, said two leaf spring latch members respectively confronting said two internal surfaces of said reference side member.

* * * * *